US008908938B2

(12) United States Patent
Gündel

(10) Patent No.: US 8,908,938 B2
(45) Date of Patent: Dec. 9, 2014

(54) METHOD AND DEVICE FOR PROVIDING A SEGMENTED VOLUME DATA RECORD FOR A VIRTUAL COLONOSCOPY, AND COMPUTER PROGRAM PRODUCT

(75) Inventor: Lutz Gündel, Erlangen (DE)

(73) Assignee: Siemens Aktiengesellschaft, Munich (DE)

( * ) Notice: Subject to any disclaimer, the term of this patent is extended or adjusted under 35 U.S.C. 154(b) by 1122 days.

(21) Appl. No.: 12/836,069

(22) Filed: Jul. 14, 2010

(65) Prior Publication Data

US 2011/0013815 A1    Jan. 20, 2011

(30) Foreign Application Priority Data

Jul. 16, 2009  (DE) .................. 10 2009 033 452

(51) Int. Cl.
*G06K 9/00* (2006.01)
*A61B 5/055* (2006.01)
*A61B 5/00* (2006.01)

(52) U.S. Cl.
CPC .............. *A61B 5/055* (2013.01); *A61B 5/4255* (2013.01)
USPC ........................................ 382/128

(58) Field of Classification Search
USPC ........................................ 382/128
See application file for complete search history.

(56) References Cited

U.S. PATENT DOCUMENTS

| 8,023,703 B2 * | 9/2011 | Franaszek et al. ............ 382/128 |
| 2007/0003131 A1 | 1/2007 | Kaufman |
| 2007/0073114 A1 | 3/2007 | Gundel |
| 2007/0276225 A1 * | 11/2007 | Kaufman et al. ............ 600/416 |

FOREIGN PATENT DOCUMENTS

| DE | 102005046385 A1 | 4/2007 |
| DE | 102007056800 A1 | 6/2009 |
| DE | 102007058687 A1 | 6/2009 |
| WO | WO 2005101314 A2 | 10/2005 |
| WO | WO 2007064980 A2 | 6/2007 |

* cited by examiner

*Primary Examiner* — Neal Sereboff
*Assistant Examiner* — Maroun Kanaan
(74) *Attorney, Agent, or Firm* — Harness, Dickey & Pierce, P.L.C.

(57) ABSTRACT

A method and a device are disclosed for providing a segmented volume data record for a virtual colonoscopy, the volume data record having image information relating to the intestines of a creature, which intestines have been labeled by a first and a second contrast agent. In at least one embodiment, voxels representing the first contrast agent, voxels representing stool remains labeled by the second contrast agent and voxels representing intestinal tissue are segmented, the segmentation taking place in a volume data record recorded of the body region of the creature having the intestines, which have been labeled by a first and a second contrast agent. In at least one embodiment, at least sections of the intestinal wall are displayed on the basis of the segmentation in the virtual colonoscopy, even if these sections of the intestinal wall are, in the segmented volume data record, covered by stool remains labeled by the second contrast agent. Further, a computer program product having a computational program for carrying out the method is also disclosed.

21 Claims, 3 Drawing Sheets

# METHOD AND DEVICE FOR PROVIDING A SEGMENTED VOLUME DATA RECORD FOR A VIRTUAL COLONOSCOPY, AND COMPUTER PROGRAM PRODUCT

PRIORITY STATEMENT

The present application hereby claims priority under 35 U.S.C. §119 on German patent application number DE 10 2009 033 452.1 filed Jul. 16, 2009, the entire contents of which are hereby incorporated herein by reference.

FIELD

At least one embodiment of the invention generally relates to a method and/or a device for providing a segmented volume data record for a virtual colonoscopy, which volume data record has image information relating to the intestines of a creature, which intestines have been labeled by a first and a second contrast agent. At least one embodiment of the invention moreover generally relates to a computer program product having a computational program executing the method.

BACKGROUND

Virtual colonoscopy is a non-invasive method, in particular for examining the large intestine of a patient on the basis of image information relating to the large intestine, which image information was obtained, for example, by a magnetic resonance scanner or an X-ray computed tomography scanner. Prior to recording the image information relating to the large intestine, a contrast agent, e.g. air or carbon dioxide in the case of X-ray computed tomography imaging or water in the case of magnetic resonance imaging, is generally applied rectally into the large intestine of the patient so that the large intestine unfolds.

Furthermore, the large intestine is generally also freed of stool remains prior to the recording of image information, because only this allows meaningful diagnosis of the interior wall of the large intestine. However, patients often perceive precisely this removal of stool remains to be uncomfortable and so methods are preferred in which the removal of stool remains is avoided to a great extent or at least is less uncomfortable.

One method of avoiding too rigorous removal of stool remains from the large intestine prior to recording image information is the digital subtraction of marked stool from a volume data record having image information relating to the intestines. The stool remains are marked by a contrast agent, which is generally dispensed orally to the respective patient and can be easily detected in the utilized imaging method.

By way of example, barium was found to be a suitable contrast agent for X-ray computed tomography. The dispensed barium and the remaining stool mix in the large intestine until the recording of the image information. This procedure is also referred to as stool tagging, i.e. the labeling or marking of the stool. The stool-barium mixture has CT values of greater than 200 Hounsfield units in the volume data record of the imaging method, which values can be easily recognized. By way of example, the recognition can be brought about by means of a thresholding method. The image voxels representing the stool-barium mixture, identified with the aid of the thresholding method, ultimately obtain a CT value of approximately −1000 Hounsfield units, which corresponds to the CT value of the rectally administered air and is referred to as digital subtraction.

What are problematic in this method are, in particular, the transitions between stool-barium mixture and air and between stool-barium mixture and intestinal tissue. There are also transitions in the CT values here, and so the affected voxels cannot be assigned unambiguously to one of the following groups: intestinal tissue, stool-barium mixture or air. An additional difficulty is that the remaining stool and the barium often do not mix homogeneously.

Therefore, undesired structures that have the shape of intestinal polyps sometimes remain in the volume data record after the digital subtraction. Such structures remaining in the volume data record can accordingly lead to false diagnoses. Secondly, fine structures, such as intestinal folds, can be subtracted by mistake in the digital subtraction, and so a lesion, should it be located there, cannot be diagnosed.

SUMMARY

In at least one embodiment, a method and/or a device are disclosed such that a volume data record for a virtual colonoscopy can be provided, in which the risk of a false interpretation is avoided to the greatest possible extent. Furthermore, a corresponding computer program product is also specified.

According to at least one embodiment of the invention, a method is disclosed for providing a segmented volume data record for a virtual colonoscopy, which volume data record has image information relating to the intestines of a creature, wherein the intestines have been labeled by a first and a second contrast agent. Whilst the first contrast agent is provided for unfolding the intestines, the second contrast agent is used to mark the stool remains in the intestines. In a measured volume data record, which is a recording of the body region of the creature and includes the intestines labeled by a first and a second contrast agent, voxels representing the first contrast agent, voxels representing stool remains preferably labeled homogeneously by the second contrast agent and voxels representing intestinal tissue are segmented and identified, which voxels are part of the volume data record. At least sections of the intestinal wall are displayed on the basis of the segmented volume data record in the virtual colonoscopy, even if these sections of the intestinal wall are covered in the segmented volume data record by stool remains labeled by the second contrast agent, because the segmented voxels representing stool remains labeled by the second contrast agent are not used for imaging.

Thus, there is no digital subtraction of stool remains out of the volume data record in at least one embodiment of the present invention, as a result of which the disadvantages of false or undesired subtraction mentioned at the outset are avoided. Rather, the volume data record is segmented or the voxel values of the volume data record are determined such that voxels representing the first contrast agent, voxels representing stool remains labeled by the second contrast agent and voxels representing intestinal tissue can clearly be distinguished from one another. The advantage of this is that a so-called virtual flight through the segmented volume data record can take place in the virtual colonoscopy and the intestinal wall can be visualized despite still being partly covered by stool remains marked by the second contrast agent because the voxel values of the stool remains marked with the second contrast agent, which voxel values are known from the segmentation, can be ignored for the imaging. Thus, it is virtually possible to see through these stool remains.

In the case of a visualization method such as e.g. the surface-shaded display, the voxel thresholds for visualizing the intestinal wall are fixed on the basis of the segmentation e.g. such that a voxel value assigned to the intestinal wall is used for visualizing the intestinal wall, while a voxel value assigned to marked stool is skipped, i.e. not used for the visualization. Accordingly, if a voxel value assigned to marked stool remains and a voxel value assigned to the intestinal wall are situated one behind the other along an observer beam, the voxel value assigned to the marked stool remains is skipped, or an interrupt criterion for the visualization does not take effect. Only once a voxel value assigned to the intestinal wall is registered does the interrupt criterion take effect and this voxel value is used for the visualization.

According to one variant of at least one embodiment of the invention, there is also a segmentation of the voxels representing the transitions between the first contrast agent and stool remains labeled by the second contrast agent and/or the voxels representing the transitions between the first contrast agent and intestinal tissue and/or the voxels representing the transitions between stool remains labeled by the second contrast agent and intestinal tissue in order to improve the visualization of the intestinal wall for the virtual colonoscopy.

According to one embodiment of the invention, the segmentation can be brought about using a thresholding method, by way of region growing, using the watershed algorithm, using a three-dimensional modification of the watershed algorithm and/or by means of a dilatation. Here, the various segmentation methods can be applied individually or in combination.

An upper threshold is fixed for a first component or voxels representing a first tissue type, and a lower threshold is fixed for a second component or voxels representing a second tissue type in a three-dimensional modification of the watershed algorithm. Subsequently, the upper threshold is lowered, preferably continuously, and the lower threshold is raised correspondingly, preferably continuously, with that voxel value at which the lowered upper threshold and the raised lower threshold meet being fixed as the segmentation boundary between the first component or the first tissue type and the second component or the second tissue type.

According to an embodiment of the invention, those segmented voxels representing the first contrast agent that cannot be assigned to the interior of the intestines are firstly removed from the measured volume data record. By way of example, if the first contrast agent is air and if the measured volume data record contains image information relating to the lungs of the patient or if the measured volume data record contains air components situated outside of the patient, these are removed from the measured volume data record.

A further embodiment of the invention provides for those segmented voxels that represent the first contrast agent and that are assigned to the interior of the intestines to form at least one first partial volume. Ideally, there is only one first partial volume. However, it is possible for the volume of the first contrast agent to be interrupted, for example by an agglomeration of stool remains, and hence for there to be two or even more partial volumes of the first contrast agent.

According to a variant of at least one embodiment of the invention, voxels representing bones and/or voxels representing image noise, which voxels are in the measured volume data record, are segmented and are preferably likewise removed from the measured volume data record because these are not required for the virtual colonoscopy and have a distracting effect.

According to a further variant of at least one embodiment of the invention, the voxels representing stool remains that have not been labeled homogeneously by the second contrast agent are segmented and are assigned to the voxels representing stool remains labeled, preferably homogeneously, by the second contrast agent because there is no need for a distinction to be made between stool remains that have not been labeled homogeneously by the second contrast agent and stool remains that have been labeled homogeneously by the second contrast agent. The voxels representing stool remains labeled by the second contrast agent preferably form at least one second partial volume. As far as the stool remains are concerned, there will however generally be a plurality of second partial volumes because the assumption can be made that stool remains remain in the intestines at a number of positions independently of one another.

According to one variant of at least one embodiment of the invention, the at least one first partial volume and/or at least one second partial volume adjoining the at least first partial volume is dilated, i.e. defined and extended by the addition of voxels in a targeted fashion, by a prescribable or prescribed number of voxels in order to determine the voxels representing the transitions between the first contrast agent and stool remains labeled by the second contrast agent.

According to one embodiment of the invention, those voxels of the prescribable or prescribed number of voxels that interconnect the at least one first partial volume and the at least one second partial volume are identified as voxels of a transition between the first contrast agent and stool remains labeled by the second contrast agent. According to a further embodiment of the invention, a third partial volume is formed by the at least one first partial volume, the at least one second partial volume and the identified voxels from the transitions between the first contrast agent and stool remains labeled by the second contrast agent.

According to a variant of at least one embodiment of the invention, the voxels representing the transitions between the first contrast agent and intestinal tissue and/or the voxels representing the transitions between stool remains labeled by the second contrast agent and intestinal tissue are segmented or identified by the third partial volume likewise being dilated at its edges, i.e. defined and extended at the edges by the addition of voxels in a targeted fashion, by a prescribable or prescribed number of voxels.

At least one view of the interior of the intestines can now be reconstructed in the virtual colonoscopy on the basis of the segmentation using the surface-shaded display method according to a further variant of at least one embodiment of the invention. In general, a multiplicity of views of the interior of the intestines, more particularly of the intestinal wall, are generated within the scope of virtual colonoscopy, i.e. during the virtual flight through the intestines.

Here, starting at an observer position in the intestines, beams are preferably emitted from the observer position and that voxel is illustrated in each case that is situated on a beam and the voxel value of which exceeds a prescribed voxel threshold assigned to the intestinal wall, even if the intestinal wall in the segmented volume data record is covered by stool remains labeled by the second contrast agent.

A device having a computational arrangement designed to carry out one of the above-described methods is also disclosed. For this, the computational arrangement has an appropriate computational program or software or software modules, which can carry out the segmentation and the virtual colonoscopy.

The computer program product according to at least one embodiment of the invention has a computational program stored on a data storage medium that can be read by a computational arrangement in order to carry out or control one of the above-described methods when the computational program has been loaded into the computational arrangement.

BRIEF DESCRIPTION OF THE DRAWINGS

An example embodiment of the invention is displayed in the attached schematic drawings, in which.

DETAILED DESCRIPTION OF THE EXAMPLE EMBODIMENTS

Figure 1:
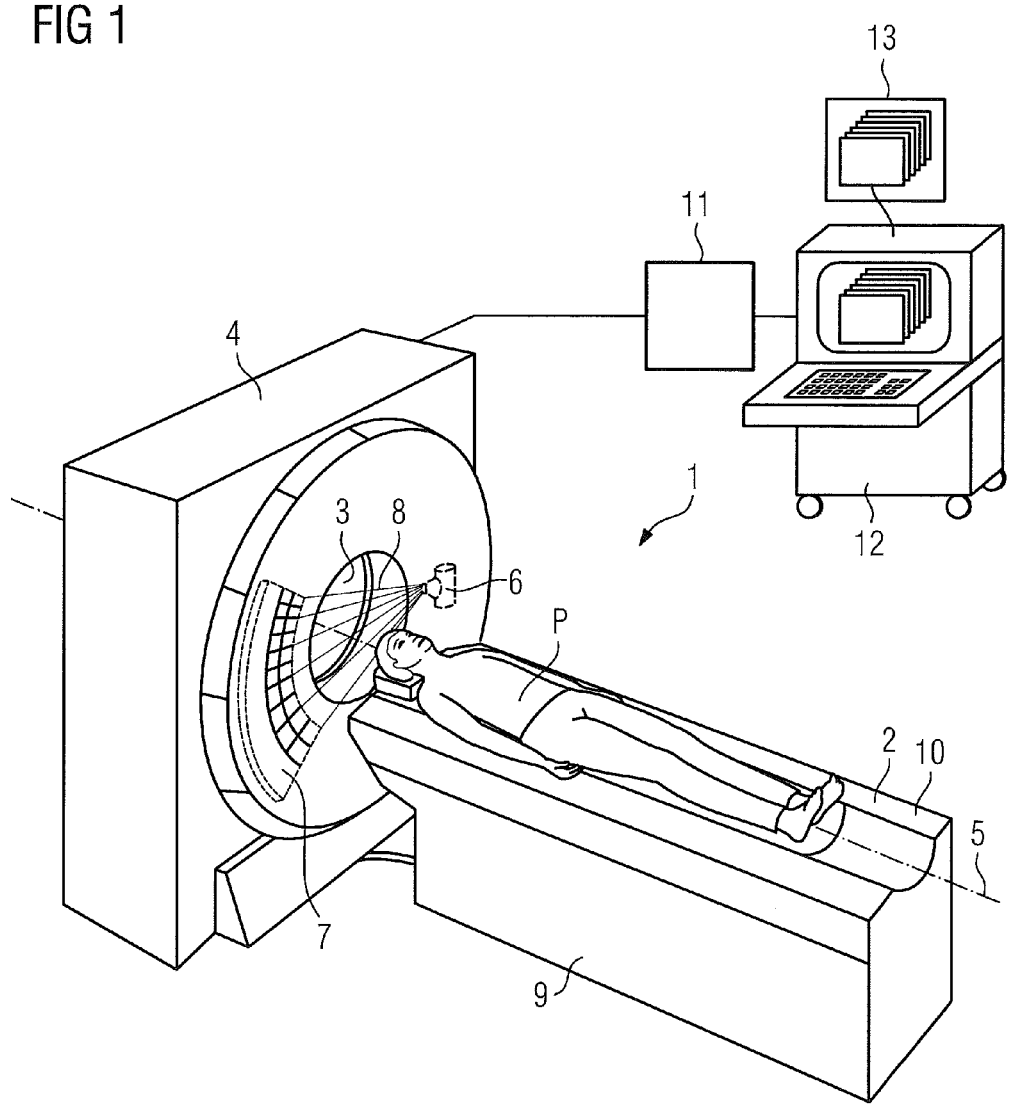
FIG. 1 shows an X-ray computed tomography scanner for generating a volume data record connected to a computational arrangement.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

In the figures, equivalent or functionally equivalent elements, components, tissues, etc. are always provided with the same reference signs. The illustrations in the figures are schematic and not necessarily true to scale, with it being possible for the scale to vary between figures. In the following text, and without loss of generality, the X-ray computed tomography scanner 1 illustrated in FIG. 1 is only addressed to the extent considered necessary for understanding embodiments of the invention.

The X-ray computed tomography scanner 1 shown in figure has a patient couch 2 for supporting a patient P to be examined. The X-ray computed tomography scanner 1 furthermore comprises a gantry 4 with a tube-detector system mounted such that it can rotate about a system axis 5. The tube-detector system has an X-ray tube 6 and an X-ray detector unit 7 that mutually oppose one another. During operation, X-ray radiation 8 is emitted from the X-ray tube 6 in the direction of the X-ray detector unit 7 and registered by the latter.

The patient couch 2 has a couch base 9, on which there is arranged a patient support table 10 provided to actually support the patient P. The patient support table 10 can be adjusted relative to the couch base 9 such that the patient support table 10 with the patient P can be inserted into the opening 3 of the gantry 4 for the purpose of recording 2D X-ray projections of the patient P, for example in a spiral scan. The computational processing of the 2D X-ray projections or the reconstruction of a volume data record of a body region of the patient P on the basis of the 2D X-ray projections is performed by a schematically illustrated image computer 11 of the X-ray computed tomography scanner 1.

The image computer 11 of the X-ray computed tomography scanner 1 is connected to a computational arrangement 12, by which a virtual colonoscopy of the large intestine of the patient P should be carried out in the case of the present example embodiment of the invention. For this, the computational arrangement 12 is provided with an appropriate computational program 13, which, in the present case, was loaded into the computational arrangement 12 with the aid of a portable storage medium, for example a CD, and which has program segments or modules for segmenting a volume data record and program segments or modules for a so-called virtual flight through image information relating to the large intestine contained in the segmented volume data record for examining the interior wall of the large intestine.

In order to prepare obtaining a volume data record of the body region of the patient P comprising the large intestine, the patient is provided with two contrast agents. A first contrast agent in the form of air is applied rectally to the patient P so that the large intestine unfolds. A second contrast agent in the form of barium is dispensed orally to the patient. Here, the barium that has advanced into the large intestine mixes with stool remains remaining in the large intestine of the patient P, which stool remains were not removed in the course of removing stool from the large intestine by the patient P ingesting a liquid, and the barium marks the stool remains. In this context, this is also referred to as stool tagging. The sequence in which the two contrast agents are dispensed to the patient P and the temporal interval between dispensing the two contrast agents are unimportant to embodiments of the present invention.

Once the patient P or the large intestine of the patient P has been provided with the air and the barium, the X-ray computed tomography scanner 1 is firstly used in a conventional fashion to reconstruct a volume data record 14 of the body region comprising the large intestine of the patient P, which volume data record is provided for the computational arrangement 12. In the case of the present example embodiment of the invention, the further method steps are carried out by the computational arrangement 12.

In preparation of a virtual flight through the image information relating to the large intestine contained in the volume data record 14, the volume data record 14 is segmented. During the segmentation, the voxels of the volume data record 14 are assigned to certain components or are classified for the subsequent imaging of the interior of the large intestine. In the case of the present example embodiment of the invention, the essential components, which are of importance for the virtual colonoscopy of the large intestine, are illustrated in FIG. 2 that shows a schematic cross section through the large intestine.

Figure 2:
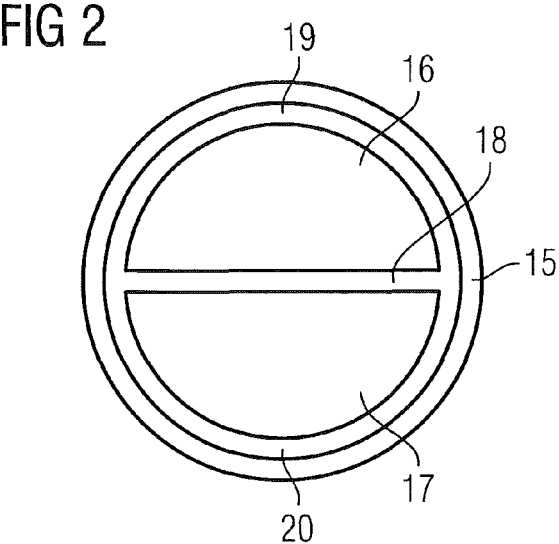
FIG. 2 shows a schematic cross section through the intestines of a patient.

In FIG. 2, the large intestine tissue is provided with the reference sign 15. The first contrast agent air 16 and stool remains 17 marked with the second contrast agent barium are in the interior of the large intestine. Moreover, there are transitions 18 between air 16 and marked stool remains 17, transitions 19 between air 16 and intestinal tissue 15 and transitions 20 between marked stool remains 17 and intestinal tissue 15.

Figure 3:
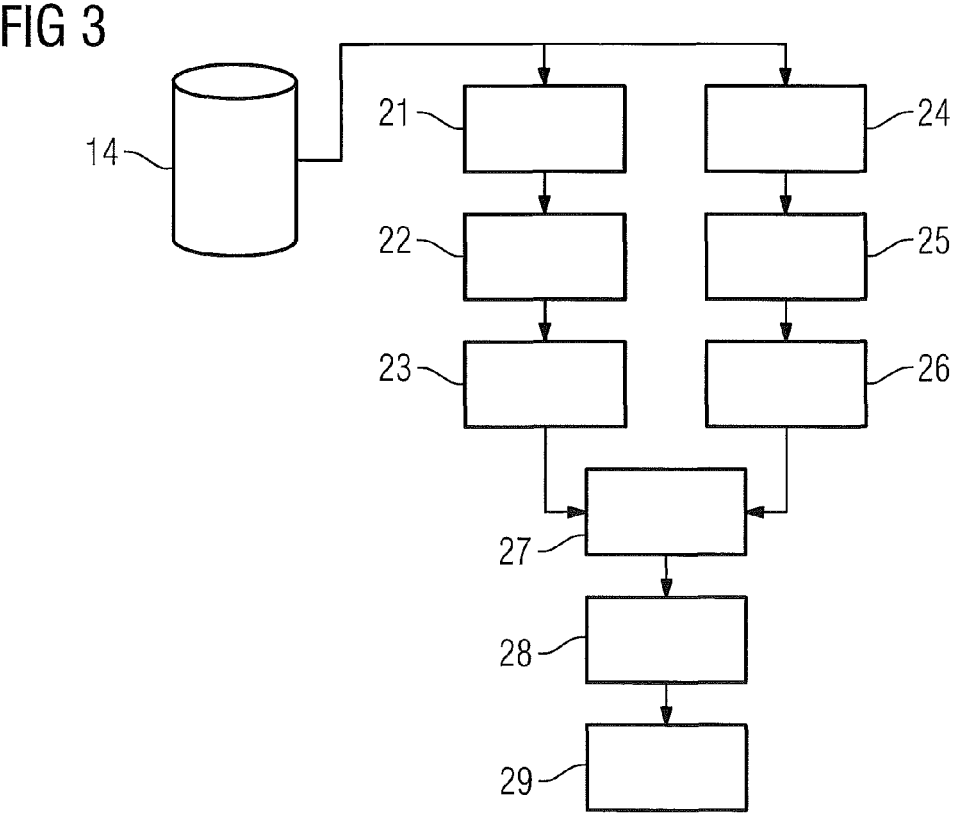
FIG. 3 shows a demonstration of the procedure when segmenting a volume data record.

The steps for segmenting the mentioned components are illustrated in FIG. 3. In a first segmentation step 21, all voxels of the volume data record 14 representing air, the CT value of which lies below the threshold of −800 Hounsfield units, are identified by way of e.g. a thresholding method. In a method step 22, all voxels representing air situated outside of the body of the patient P, and accordingly representing ambient air, are eliminated from the volume data record. In a further method step 23, all voxels that represent air, which voxels are situated outside of the large intestine despite being situated within the body of the patient P and hence can be assigned to the lungs of the patient P, are likewise eliminated from the volume data record.

As a result, this obtains all voxels that represent air and are assigned to the interior of the large intestine. Ideally, all voxels that represent air and are assigned to the interior of the large intestine form a first partial volume. However, it is also possible for there to be a plurality of first partial volumes, if individual partial volumes of air are separated from one another by e.g. an agglomeration of stool remains or a piece of the large intestine that has not completely unfolded. In the following text the assumption is made that there is only one first partial volume air in the volume data record 14.

In the case of the present example embodiment of the invention, voxels with high CT values are sought after in the volume data of the volume data record 14 in parallel to the identification of the voxels assigned to the large intestine and representing air. More particularly, voxels representing stool remains marked with barium and voxels representing bones are identified in a method step 24, for example by using a thresholding method or by applying the watershed algorithm.

In a method step 25, voxels representing image noise are likewise detected by the application of a thresholding method or by applying the watershed algorithm, and these voxels are removed from the volume data record 14 together with the identified voxels representing bones.

In a method step 26 referred to as homogenizing, voxels representing stool remains that have not been mixed homogeneously with barium are identified by merely the region-growing method, merely applying the watershed algorithm or in combination with a dilatation, and are assigned to the aforementioned voxels representing stool remains marked by barium. The voxels representing stool remains marked by barium form at least one second partial volume. The voxels representing stool remains marked by barium usually form a plurality of second partial volumes because stool remains generally agglomerate independently of one another at a plurality of sections of the wall of the large intestine.

By the way, the watershed algorithm for the segmentation can also be used in a three-dimensional modification. This allows a three-dimensional visualization of the CT values of the volume data record and a type of CT-value "mountain range" is obtained. In its normal application, the algorithm would clearly fill these mountains step by step with liquid and construct dams at those places at which the liquids from two valleys would flow into one another. The constructed dams would represent the object, tissue or material boundaries.

In the modification, an upper threshold, e.g. for voxels representing stool remains homogeneously marked by barium, and a lower threshold, e.g. for voxels representing stool remains not marked homogeneously by barium, are fixed. Clearly, the upper threshold and the lower threshold define two different basins for stool remains not marked homogeneously by barium and stool remains marked homogeneously by barium, wherein the basin for stool remains not marked homogeneously by barium is empty and the basin for stool remains marked homogeneously by barium is filled with liquid. Subsequently, the upper threshold is lowered, preferably continuously, and the lower threshold is raised, preferably continuously. Clearly, the basin for stool remains not marked homogeneously by barium is filled, preferably continuously, with liquid, while the basin for stool remains marked homogeneously by barium filled with liquid is emptied continuously. The place at which the basins have the same level, or that CT value at which the lowered upper threshold and the raised lower threshold meet, fixes the segmentation boundary between voxels representing stool remains not marked homogeneously by barium and voxels representing stool remains marked homogeneously by barium.

Continuing the segmentation, the transitions between air and voxels representing marked stool remains are identified in the volume data record in a step 27. For this, the first partial volume and/or the second partial volumes are each dilated, i.e. extended at the edges by a predetermined number of voxels in a targeted and defined fashion, by a predetermined number of voxels. If this connects the first partial volume to a second partial volume, the added voxels or the voxels from the dilatation belong to the voxels representing a transition 18 between air 16 and marked stool remains 17.

By the way, the three-dimensional modification of the watershed algorithm can also be used for determining the segmentation boundaries between air 16 and marked stool remains 17. In this case, an upper threshold for voxels representing stool remains marked by barium and a lower threshold for voxels representing air are fixed. Clearly, the upper threshold and the lower threshold again define two different basins for stool remains marked with barium and for air, wherein the basin for stool remains marked by barium is filled with liquid and the basin for air is empty. Subsequently, the upper threshold is lowered, preferably continuously, and the lower threshold is raised, preferably continuously. Clearly, the basin for air is filled, preferably continuously, with liquid while the basin for stool remains marked by barium filled with liquid is emptied continuously. The place at which the basins have the same level, or that CT value at which the lowered upper threshold and the raised lower threshold meet, fixes the segmentation boundary between voxels representing air and voxels representing stool remains marked by barium.

In a method step 28, the first partial volume, the second partial volumes and the segmented voxels representing a transition 18 between air 16 and marked stool remains 17 are combined to form a third partial volume. In a method step 29, this third partial volume is dilated, i.e. extended at its edges by a predetermined number of voxels in a targeted and defined fashion, in order to segment or identify the transitions 19 between air 16 and intestinal tissue 15 and the transitions 20 between marked stool remains 17 and intestinal tissue 15. In this fashion, the voxels representing the transitions 19 and 20, or the voxels assigned to the transitions 19 and 20, are segmented or identified.

Figure 4:
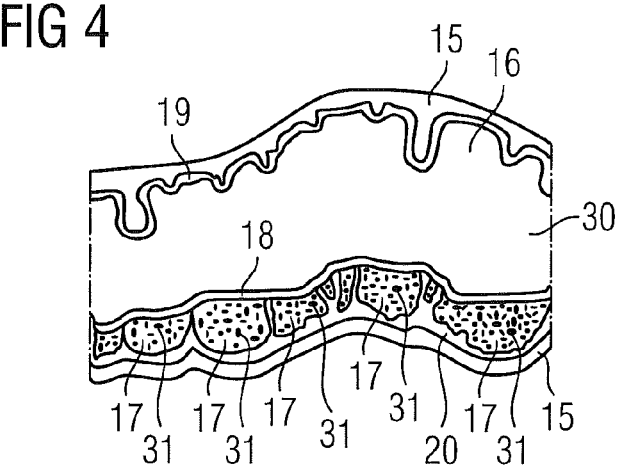
FIG. 4 shows a segmented intestine section in a patient.

Thus, the originally reconstructed measured volume data record 14 has been segmented in steps according to the above-described procedure, and so a segmented volume data record having image information relating to the large intestine of the patient P now is present in the computational arrangement 12 for a virtual colonoscopy. FIG. 4 shows a section of a segmented section of the intestines of the patient P in an exemplary fashion. In FIG. 4 it is possible to recognize the first partial volume 30 having air 16, a plurality of second partial volumes 31 having marked stool remains 17, transitions 18 between air 16 and marked stool remains 17, transitions 19 between air 16 and the intestinal wall 15 and transitions 20 between marked stool remains 17 and the intestinal wall 15.

The central line through the large intestine is firstly determined for the virtual colonoscopy in the segmented volume data record on the basis of the segmented volume data record, with progress being made along the central line in order to diagnose the inner intestinal wall. The central line virtually constitutes a path, which is also referred to as the flight path for the so-called virtual flight through the large intestine, wherein there can also be deviations from the central line M.

Figure 5:
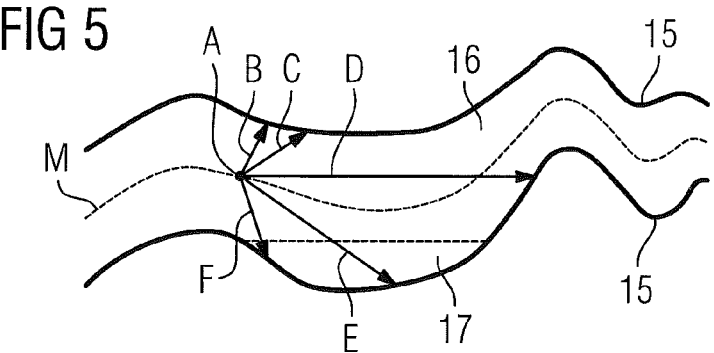
FIGS. 5 and 6 show a demonstration of the visualization of the intestinal wall on the basis of the segmentation.

Whilst progressing along the central line M, views of the interior side of the large intestine are generated using the surface-shaded display method in the case of the present exemplary embodiment of the invention, as illustrated in FIG. 5. Herein, beams are emitted in a multiplicity of directions B to F from selected or assumed observer positions, e.g. the current position A of a virtual colonoscope. If the CT value of a voxel, which is situated along a beam or hit by a beam, exceeds a predetermined voxel threshold assigned to the intestinal wall 15, the voxel value of this voxel is used for the imaging at the respective observer position.

In the example shown in FIG. 5, the beams B to D firstly only hit voxels representing air 16, the voxel or CT values of which are known from the segmentation and lie below the voxel threshold. Only once the beams B to D are incident on the intestinal wall 15 is the respectively specified voxel threshold exceeded and the respective voxel or CT value of the voxel representing the intestinal wall 15 used for imaging at the observer position A. Beams E and F firstly also only run through voxels representing air 16 and are then incident on voxels representing marked stool remains 17, the voxel or CT values of which are likewise known from the segmentation. It is for this reason that there is no interrupt here, but there is further progress along beam E or beam F, and there is only an interrupt once the prescribed voxel threshold is exceeded by a voxel or CT value of a voxel representing the intestinal wall, which voxel or CT value is ultimately used for the imaging. As a result of the segmentation and the prescribed voxel threshold, stool remains 17 marked with barium are therefore invisible in the imaging.

Figure 6:
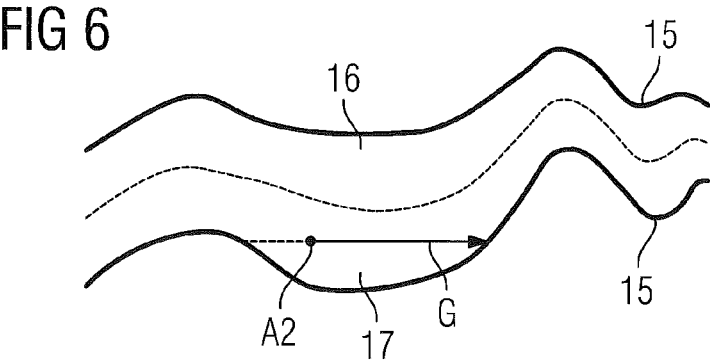

A special case will still be described on the basis of FIG. 6, in which a beam G emitted by an observer position A2 runs along the boundary surface between air 16 and marked stool remains 17. The partial volume effect can cause the predetermined voxel threshold to be already exceeded before the intestinal wall, and so there is no transparency here. However, in the case of virtual colonoscopy, this is not a completely undesirable effect. Rather, this visualizes the surface of marked stool remains. This is comparable to a diver wearing diving goggles, whose diving goggles are only partly submerged in the water, i.e. the diver can see clearly both above and below the water surface, with the water surface being noticed as a thin line. Accordingly, the present imaging visualizes the intestinal wall below and above the surface of marked stool remains, and the surface is visualized as a thin line.

Embodiments of the invention were described above using the example of a volume data record of the large intestine of a patient generated using an X-ray computed tomography scanner. However, the volume data record can also be generated by a magnetic resonance imaging scanner.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A method for providing a segmented volume data record for a virtual colonoscopy, the volume data record including image information relating to the intestines of a creature, the method comprising:

emitting beams from an observer position in the intestines;
labeling, by one or more processors, the intestines by using a first and a second contrast agent, voxels representing stool remains being labeled by the second contrast agent;
segmenting, by the one or more processors, voxels representing intestinal tissue, the segmentation taking place in a volume data record recorded of the body region of the creature including the intestines, labeled by the first and the second contrast agent; and
displaying, by the one or more processors, without digital subtraction of the stool remains labeled by the second contrast agent, at least sections of an intestinal wall of the intestines on the basis of the segmentation in the virtual colonoscopy, when the sections of the intestinal wall are, in the segmented volume data record, covered by stool remains labeled by the second contrast agent, the displaying including,
reconstructing at least one view of an interior of the intestines using a surface-shaded display in the virtual colonoscopy based on the segmented volume data record, the reconstructing beginning from the observer position in the intestines and including,
determining if the intestinal wall in the segmented volume data record is covered by stool remains labeled by the second contrast agent,
illustrating at least one image voxel on the beams when a voxel value of an associated image voxel exceeds a voxel threshold assigned to the intestinal wall when the intestinal wall in the segmented volume data record is covered by stool remains labeled by the second contrast agent, and
illustrating the at least one image voxel on the beams when the voxel value of the associated image voxel exceeds the voxel threshold assigned to the intestinal wall when the intestinal wall in the segmented volume data record is not covered by stool remains labeled by the second contrast agent.

2. The method as claimed in claim 1, wherein the segmentation of the voxels represents at least one of:
transitions between the first contrast agent and stool remains labeled by the second contrast agent;
transitions between the first contrast agent and the intestinal tissue; and
transitions between stool remains labeled by the second contrast agent and the intestinal tissue.

3. The method as claimed in claim 2, wherein the segmentation is brought by at least one of:
using a thresholding method;
region growing;
using a watershed algorithm;
using a three-dimensional modification of the watershed algorithm; and
way of a dilatation.

4. The method as claimed in claim 3, wherein an upper threshold is fixed for a first component or voxels representing a first tissue type and a lower threshold is fixed for a second component or voxels representing a second tissue type in a three-dimensional modification of the watershed algorithm, wherein the upper threshold is lowered and the lower threshold is raised, and wherein a voxel value at which the lowered upper threshold and the raised lower threshold meet is fixed as the segmentation boundary between the first component or the first tissue type and the second component or the second tissue type.

5. The method as claimed in claim 1, wherein the segmentation is brought by at least one of:
   using a thresholding method;
   region growing;
   using a watershed algorithm;
   using a three-dimensional modification of the watershed algorithm; and
   way of a dilatation.

6. The method as claimed in claim 5, wherein an upper threshold is fixed for a first component or voxels representing a first tissue type and a lower threshold is fixed for a second component or voxels representing a second tissue type in a three-dimensional modification of the watershed algorithm, wherein the upper threshold is lowered and the lower threshold is raised, and wherein a voxel value at which the lowered upper threshold and the raised lower threshold meet is fixed as the segmentation boundary between the first component or the first tissue type and the second component or the second tissue type.

7. The method as claimed in claim 1, wherein segmented voxels labeled by the first contrast agent that cannot be assigned to the interior of the intestines are removed from the volume data record.

8. The method as claimed in claim 1, wherein segmented voxels labeled by the first contrast agent and assigned to the interior of the intestines form at least one first partial volume.

9. The method as claimed in claim 1, wherein at least one of voxels representing bones and voxels representing image noise, which voxels are in the volume data record, are segmented.

10. The method as claimed in claim 9, wherein at least one of the segmented voxels representing bones and the voxels representing image noise are removed from the volume data record.

11. The method as claimed in claim 1, wherein the voxels representing stool remains that have not been labeled homogeneously by the second contrast agent are segmented and are assigned to the voxels representing stool remains labeled by the second contrast agent.

12. The method as claimed in claim 1, wherein the voxels representing stool remains labeled by the second contrast agent form at least one second partial volume.

13. The method as claimed in claim 12, wherein at least one of a relatively smallest first partial volume and an at least second partial volume is dilated by a number of voxels in order to determine the voxels representing the transitions between the first contrast agent and stool remains labeled by the second contrast agent.

14. The method as claimed in claim 13, wherein the voxels of the number of voxels that interconnect the at least one first partial volume and the at least one second partial volume are identified as voxels of a transition between the first contrast agent and stool remains labeled by the second contrast agent.

15. The method as claimed in claim 14, wherein a third partial volume is formed by the at least one first partial volume, the at least one second partial volume and the identified voxels from the transitions between the first contrast agent and stool remains labeled by the second contrast agent.

16. The method as claimed in claim 15, wherein at least one of the voxels representing the transitions between the first contrast agent and intestinal tissue and the voxels representing the transitions between stool remains labeled by the second contrast agent and intestinal tissue are segmented by a third partial volume being dilated at its edges by another number of voxels.

17. A device comprising:
   a computational arrangement designed to carry out the method as claimed in claim 1.

18. A non-transitory computer readable medium including a computational program stored on a data storage medium that can be read by a computational arrangement in order to carry out a method as claimed in claim 1 when the computational program has been loaded into and is executed by the computational arrangement.

19. A method for providing a segmented volume data record for a virtual colonoscopy, the volume data record having image information relating to the intestines of a creature, which intestines have been labeled by a first and a second contrast agent, the method comprising:
   emitting beams from an observer position in the intestines;
   segmenting, by one or more processors, voxels representing the first contrast agent, voxels representing stool remains labeled by the second contrast agent and voxels representing intestinal tissue, the segmentation taking place in a volume data record recorded of the body region of the creature including the intestines, labeled by the first and the second contrast agent; and
   displaying, by the one or more processors, without digital subtraction of the stool remains labeled by the second contrast agent, at least sections of an intestinal wall on the basis of the segmentation in the virtual colonoscopy, even if the sections of the intestinal wall are, in the segmented volume data record, covered by stool remains labeled by the second contrast agent, the displaying including,
   reconstructing at least one view of an interior of the intestines using a surface-shaded display in the virtual colonoscopy based on the segmented volume data record, the reconstructing beginning from the observer position in the intestines and including,
      determining if the intestinal wall in the segmented volume data record is covered by stool remains labeled by the second contrast agent,
      illustrating at least one image voxel on the beams when a voxel value of an associated image voxel exceeds a voxel threshold assigned to the intestinal wall when the intestinal wall in the segmented volume data record is covered by stool remains labeled by the second contrast agent, and
      illustrating the at least one image voxel on the beams when the voxel value of the associated image voxel exceeds the voxel threshold assigned to the intestinal wall when the intestinal wall in the segmented volume data record is not covered by stool remains labeled by the second contrast agent.

20. A device comprising:
   a computational arrangement designed to carry out the method as claimed in claim 19.

21. A non-transitory computer readable medium including a computational program stored on a data storage medium that can be read by a computational arrangement in order to carry out a method as claimed in claim 19 when the computational program has been loaded into and is executed by the computational arrangement.

* * * * *